United States Patent [19]

Leep et al.

[11] Patent Number: 5,990,045
[45] Date of Patent: *Nov. 23, 1999

[54] HERBICIDAL MIXTURES

[75] Inventors: Daniel Carl Leep; Francis T. Lichtner, both of Newark, Del.

[73] Assignee: E.I. du Pont de Nemours and Company, Wilmington, Del.

[ * ] Notice: This patent issued on a continued prosecution application filed under 37 CFR 1.53(d), and is subject to the twenty year patent term provisions of 35 U.S.C. 154(a)(2).

[21] Appl. No.: 09/171,113

[22] PCT Filed: Apr. 15, 1997

[86] PCT No.: PCT/US97/06333

§ 371 Date: Oct. 13, 1998

§ 102(e) Date: Oct. 13, 1998

[87] PCT Pub. No.: WO97/38581

PCT Pub. Date: Oct. 23, 1997

Related U.S. Application Data

[60] Provisional application No. 60/015,522, Apr. 16, 1996, and provisional application No. 60/021,365, Jun. 27, 1996.

[51] Int. Cl.$^6$ .............................. A01N 43/64; A01N 57/00
[52] U.S. Cl. ........................... 504/128; 504/127; 504/133
[58] Field of Search .................................. 504/127, 128, 504/133

[56] References Cited

FOREIGN PATENT DOCUMENTS

| 0475392 | 3/1992 | European Pat. Off. . |
| 0739893 | 10/1996 | European Pat. Off. . |
| 0766918 | 4/1997 | European Pat. Off. . |
| 9208353 | 5/1992 | WIPO . |
| 93/25081 | 12/1993 | WIPO ........................... A01N 57/20 |
| 9634528 | 11/1996 | WIPO . |

OTHER PUBLICATIONS

Makino et al, C.A.; vol. 124 (1996) 124:289581b.
Suzuki et al, C.A. vol. 126 (1997) 126:74875f.

*Primary Examiner*—Allen J. Robinson

[57] ABSTRACT

This invention relates to herbicidal mixtures comprising sulfonylureas together with glyphosate, herbicidal compositions of said mixtures, and a method for the use of said mixtures to control undesired vegetation.

12 Claims, No Drawings

HERBICIDAL MIXTURES

This application claims the benefit of U.S. Provisional Applications No. 60/015,522, filed Apr. 16, 1996; and 60/021,365, filed Jun. 27 1996.

This application is a 371 of PCT/US97/06333, filed Apr. 15, 1997.

FIELD OF THE INVENTION

The present invention relates to mixtures of herbicides that have a synergistic effect on weeds and which are safe to crop plants.

BACKGROUND OF THE INVENTION

The control of undesired vegetation is extremely important in achieving high crop efficiency. Achievement of selective control of the growth of weeds especially in such useful crops as rice, soybeans, sugar beets, corn, potatoes, wheat, barley, tomatoes and plantation crops among others is very desirable. Unchecked weed growth in such useful crops can cause significant reduction in productivity and thereby result in increased costs to the consumers. The control of undesired vegetation in noncrop areas is also important. The need for finding products that achieve such results continues to be commercially important.

Combinations of herbicides are typically used to broaden the spectrum of plant control or enhance the level of control of any given species through additive effect. Certain rare combinations surprisingly give a greater-than-additive or synergistic effect. Several such valuable combinations have now been discovered.

EP 739893-A1 discloses N-(4,6-dimethoxy-(1,3,5-triazin-2-yl)-N'-[[[3-3-fluoro-propyl)-2(3H)-thiazolylidene]amino]sulfonyl]urea as a herbicide, but this reference does not disclose its mixtures with glyphosate or their surprising utility in synergistically controlling weeds.

SUMMARY OF THE INVENTION

This invention relates to mixtures of a sulfonylurea compound of Formula I

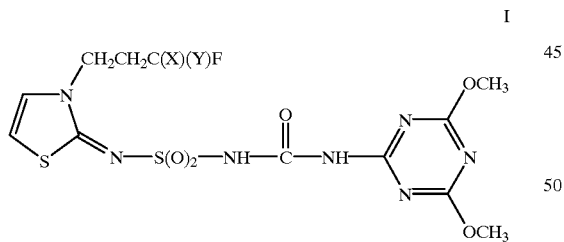

wherein X and Y are independently selected from H and F, and agriculturally suitable salts thereof with N-(phosphonomethyl)glycine (glyphosate, Formula II)

II

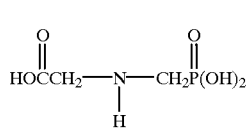

and agriculturally suitable salts thereof, which have now been discovered to synergistically control weeds. This invention also relates to herbicidal compositions comprising effective amounts of the aforesaid mixtures and at least one of the following: surfactant, solid or liquid diluent. This invention also relates to a method for controlling undesired vegetation comprising applying to the locus of the vegetation herbicidally effective amounts of the aforesaid mixtures.

Agriculturally suitable salts of N-(phosphonomethyl) glycine (Formula II) include, but are not limited to, the salts described by Formula IIa IIa

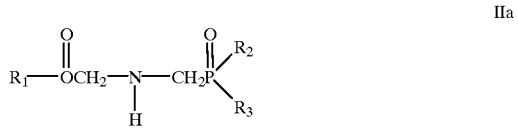

wherein $R^1$, $R^2$ and $R^3$ are independently selected from the group consisting of —OH and —OR$^4$, wherein $R^4$ is a salt-forming cation selected from the group consisting of alkali metals, alkaline earth metals, ammonium, and alkyl ammonium and mixtures thereof, provided that no more than two of $R^1$, $R^2$ and $R^3$ are —OR$^4$ when $R^4$ is ammonium or alkyl ammonium and that no more than two of $R^1$, $R^2$ and $R^3$ are —OH; $R^4$ can also be alkyl sulfonium or alkyl sulfoxonium when $R^1$ and $R^3$ are —OH. Alkyl ammonium includes mono-, di-, tri- and tetra-alkylammonium. Alkyl sulfonium means trialkylsulfonium, and alkyl sulfoxonium means trialkylsulfoxonium, where the alkyl groups are independently $C_1$–$C_3$ alkyl.

The mixtures of the invention preferred for enhanced activity include:

1. A herbicidal mixture comprising a sulfonylurea selected from N-(4,6-dimethoxy-1,3,5-triazin-2-yl)N'-[[[3-(3-fluoropropyl)-2(3H)-thiazolylidene]amino] sulfonyl]urea (Formula I, X and Y are H), N-(4,6-dimethoxy-1,3,5-triazin-2-yl)-N'-[[[(3-(3,3,3-trifluoropropyl)-2(3H)-thiazolylidene]amino]sulfonyl] urea (Formula I, X and Y are F) and N-[[[3-(3,3-difluoropropyl)-2(3H)-thiazolylidene]amino]sulfonyl]-N'-(4,6dimethoxy-1,3,5-triazin-2-yl)urea (Formula I, X is H and Y are F) together with the mono (isopropylammonium) salt of N-(phosphonomethyl) glycine (Formula II) having the common name glyphosate-isopropylammonium.

2. A herbicidal mixture comprising a sulfonylurea selected from N-(4,6-dimethoxy-1,3,5-triazin-2-yl)-N'-[[[3-(3-fluoropropyl)-2(3H)-thiazolylidene]amino] sulfonyl]urea (Formula I, X and Y are H), N-(4,6-dimethoxy-1,3,5-triazin-2-yl)-N'-[[[3-(3,3,3-trifluoropropyl)-2(3H)-thiazolylidene]amino]sulfonyl] urea (Formula I, X and Y are F) and N-[[[3-(3,3-difluoropropyl)-2(3H)-thiazolylidene]amino]sulfonyl]-N'-(4,6-dimethoxy-1,3,5-triazin-2-yl)urea (Formula I, X is H and Y are F) together with the mono (trimethylsulfonium) salt of N-(phosphonomethyl) glycine (Formula II) having the common name glyphosate-trimesium.

The mixtures of the invention most preferred for enhanced activity include:

1. A herbicidal mixture comprising N-(4,6-dimethoxy-1, 3,5-triazin-2-yl) -N'-[[[3-(3-fluoropropyl)-2(3H)-thiazolylidene]amino]sulfonyl]urea (Formula I, X and Y are H) together with the mono (isopropylammonium) salt of N-(phosphonomethyl)glycine (Formula II) having the common name glyphosate-isopropylammonium.

2. A herbicidal mixture comprising N-(4,6-dimethoxy-1,3,5-triazin-2-yl) -N'-[[[3-(3-fluoropropyl)-2(3H)-thiazolylidene]amino]sulfonyl]urea (Formula I, X and Y are H) together with the mono (trimethylsulfonium) salt of N-(phosphonomethyl)glycine (Formula II) having the common name glyphosate-trimesium.

For reason of weed control spectrum and/or crop selectivity, the preferred crops for application of the mixtures of this invention are sugar beet lines, varieties and cultivars containing at least one gene that confers tolerance to herbicides containing N-(phosphonomethyl)glycine or an agriculturally suitable salt as the active ingredient.

DETAILS OF THE INVENTION

The sulfonylureas of Formula I can be prepared as described in EP 592676-A1, WO 95/18806 (and its English language equivalent EP 739893-A1) and JP 07/330765-A. The synthesis involves the coupling of a imidothiazoline of Formula 1 with the chlorosulfonylurea of Formula 2, which in turn can be prepared from chlorosulfonyl isocyanate and the corresponding aminotriazine.

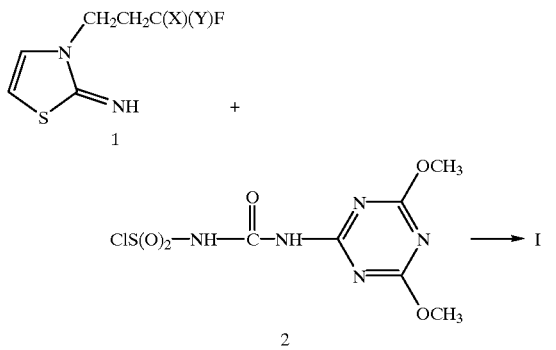

The mixtures of the present invention can include a sulfonylurea of Formula I in the form of agriculturally suitable salts thereof. These can be prepared in a number of ways known in the art. For example, metal salts can be made by contacting a sulfonylurea of Formula I with a solution of an alkali or alkaline earth metal salt having a sufficiently basic anion (e.g., hydroxide, alkoxide, carbonate or hydride). Quaternary amine salts can be made by similar techniques.

Salts of a sulfonylurea of Formula I can also be prepared by exchange of one cation for another. Cationic exchange can be effected by direct contact of an aqueous solution of a salt of a sulfonylurea of Formula I (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a sulfonylurea of Formula I (e.g., an alkali metal or quaternary amine salt) through a column packed with a cation-exchange resin containing the cation to be exchanged for that of the original salt and the desired product is eluted from the column. This method is particularly useful when the desired salt is water soluble (e.g., a potassium, sodium or calcium salt).

N-(phosphonomethyl)glycine (Formula II) and its agriculturally suitable salts, including those of Formula IIa, can be prepared by methods described in U.S. Pat. No. 4,315,765 and U.S. Pat. No. 4,405,531.

Formulation/Utility

The mixtures of the Formula I and Formula II (including Formula IIa) compounds can be formulated in a number of ways:

(a) the Formula I and Formula II compounds can be formulated separately and applied separately or applied simultaneously in an appropriate weight ratio, e.g., as a tank mix; or (b) the Formula I and Formula II compounds can be formulated together in the proper weight ratio.

Mixtures of the Formula I and Formula II compounds will generally be used in formulation with an agriculturally suitable carrier comprising a liquid or solid diluent and/or a surfactant wherein the formulation is consistent with the physical properties of the active ingredients, mode of application and environmental factors such as soil type, moisture and temperature. Useful formulations include liquids such as solutions (including emulsifiable concentrates), suspensions, emulsions (including micro-emulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredients can be (micro) encapsulated and further formed into a suspension or solid formulation; alternatively the entire formulation of active ingredient can be encapsulated (or "overcoated"). Encapsulation can control or delay release of the active ingredients. Sprayable formulations can be extended in suitable media and used at spray volumes from about one to several hundred liters per hectare. High-strength compositions are primarily used as intermediates for further formulation.

The formulations will typically contain effective amounts of active ingredients, diluent and surfactant within the following approximate ranges which add up to 100 percent by weight.

|  | Weight Percent | | |
| --- | --- | --- | --- |
|  | Active Ingredient | Diluent | Surfactant |
| Water-Dispersible and Water-soluble Granules, Tablets and Powders. | 5–90 | 0–94 | 1–15 |
| Suspensions, Emulsions, Solutions (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers*, 2nd Ed., Dorland Books, Caldwell, N.J. Typical liquid diluents are described in Marsden, *Solvents Guide*, 2nd Ed., Interscience, N.Y., 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillinite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Chemically stabilized aqueous sulfonylurea or agriculturally suitable sulfonylurea salt dispersions are taught in U.S. Pat. No. 4,936,900. Solution formulations of sulfonylureas with improved chemical stability are taught in U.S. Pat. No. 4,599,412. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering,* Dec. 4, 1967, pp 147–48, *Perry's Chemical Engineer's Handbook,* 4th Ed., McGraw-Hill, New York, 1963, pages 8–57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB No. 2,095,558 and U.S. Pat. No. 3,299,566.

For further information regarding formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science,* John Wiley and Sons, Inc., New York, 1961, pp 81–96; and Hance et al., *Weed Control Handbook,* 8th Ed., Blackwell Scientific Publications, Oxford, 1989.

In the following Examples, all percentages are by weight and all formulations are prepared in conventional ways.

Example A

High Strength Concentrate

| | |
|---|---|
| N-(4,6-dimethoxy-1,3,5-triazin-2-yl)-N'-[[[3-(3-fluoropropyl)-2(3H)-thiazolylidene]amino]sulfonyl]urea | 4.7% |
| glyphosate-isopropylammonium | 93.8% |
| silica aerogel | 0.5% |
| synthetic amorphous fine silica | 1.0%. |

Example B

Wettable Powder

| | |
|---|---|
| N-(4,6-dimethoxy-1,3,5-triazin-2-yl)-N'-[[[3-(3-fluoropropyl)-2(3H)-thiazolylidene]amino]sulfonyl]urea | 5.0% |
| glyphosate-trimesium | 60.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Example C

Granule

| | |
|---|---|
| N-(4,6-dimethoxy-1,3,5-triazin-2-yl)-N'-[[[3-(3-fluoropropyl)-2(3H)-thiazolylidene]amino]sulfonyl]urea, sodium salt | 0.8% |
| glyphosate-isopropylammonium | 9.2% |
| attapulgite granules (low volatile matter, 0.71/0.30 mm; U.S.S. No. 25–50 sieves) | 90.0%. |

Example D

Aqueous Solution Suspension

| | |
|---|---|
| N-(4,6-dimethoxy-1,3,5-triazin-2-yl)-N'-[[[3-(3-fluoropropyl)-2(3H)-thiazolylidene]amino]sulfonyl]urea | 0.1% |
| glyphosate-isopropylammonium | 24.9% |
| hydrated attapulgite | 3.0% |
| crude calciumligninsulfonate | 10.0% |
| sodium dihydrogen phosphate | 0.5% |
| water | 61.5%. |

Example E

Extruded Pellet

| | |
|---|---|
| N-(4,6-dimethoxy-1,3,5-triazin-2-yl)-N'-[[[3-(3-fluoropropyl)-2(3H)-thiazolylidene]amino]sulfonyl]urea | 0.2% |
| glyphosate-isopropylammonium | 24.8% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Example F

Wettable Powder

| | |
|---|---|
| N-(4,6-dimethoxy-1,3,5-triazin-2-yl)-N'-[[[3-(3-fluoropropyl)-2(3H)-thiazolylidene]amino]sulfonyl]urea | 0.1% |
| glyphosate-isopropylammonium | 64.9% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Example G

Extruded Pellet

| | |
|---|---|
| N-(4,6-dimethoxy-1,3,5-triazin-2-yl)-N'-[[[3-(3,3,3-trifluoropropyl)-2(3H)-thiazolylidene]amino]sulfonyl]urea | 0.6% |
| glyphosate-isopropylammonium | 24.4% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Utility

Mixtures of compounds of Formula I and Formula II (including Formula IIa) are highly active postemergent herbicides, providing unexpected synergistic control of selected grass and broadleaf weeds. Because of the efficacy of the mixtures of the present invention in controlling weeds that commonly infest sugar beet fields, they are particularly valued for their selective tolerance by sugar beet plants containing at least one gene that confers resistance to N-(phosphonomethyl)glycine and its agriculturally suitable salts. Sugar beet varieties, cultivars, and lines that have been "gene-altered" to confer resistance to N-(phosphonomethyl) glycine can be developed by a variety of methods used individually or in combination including: modification to increase biosynthesis of 5-enolpyruvyl-3-phosphoshikimate synthase, incorporation of genes encoding 5-enolpyruvyl-3-phosphoshikimate synthase with structure modified to reduce its inhibition by N-(phosphonomethyl)glycine, and incorporation of genes encoding enzymes to degrade N-phosphonmethylglycine, by methods known in the art, including those described in WO 92/00377, WO 92/04449, WO 92/06201 and WO 92,19719, U.S. Pat. No. 4,940,835, U.S. Pat. No. 4,971,908, U.S. Pat. No. 5,188,642 and U.S. Pat. No. 5,310,667.

In the context of this disclosure, a "line" is a group of plants of similar parentage that display little or no genetic variation between individuals for at least one trait. Such lines may be created by one or more generations of self-pollination and selection, or by vegetative propagation from a single parent, such as by tissue or cell culture techniques. A "variety" or "cultivar" refers to an agronomically superior line that has been extensively tested and is (or was) being used for commercial production.

The mixtures of this invention can additionally be used in combination with other commercial herbicides, insecticides or fungicides. A mixture of one or more additional herbicides with the mixtures of this invention may be particularly useful for weed control. In certain instances, combinations with other herbicides having similar spectrum of control but a different mode of action will be particularly advantageous for resistance management. Examples of other herbicides as mixture partners are: barban, bromoxynil, clodinafop, chloridazon, chlorpropham, cycloate, dalapon, desmedipham, diallate, diethatyl, endothal, EPTC, fenoxaprop, fenoxaprop-P, fluazifop, ethofumesate, glufosinate, haloxyfop, lenacil, metamitron, pebulate, phenmedipham, propham, quizalofop, sethoxydim, TCA, tralkoxydim, trifluralin and triflusulfuron methyl.

Herbicidally effective amounts of the compounds of Formula I and Formula II (or IIa) will vary depending on environmental conditions, formulation, method of application, amount and type of vegetation present, etc. The use rate ratios of Formula I to Formula II (or IIa) are in general 1:8 to 1:500, with ratios of 1:15 to 1:250 preferred for most uses. In general, the Formula I compound is applied at a rate from 1 to 30 g ai/ha and the Formula II (or IIa) compound is applied at a rate from 125 to 1500 g ai/ha. Preferably, the Formula I compound is applied at a rate from 2 to 15 g ai/ha, and the Formula II (or IIa) compound is applied at a rate from 250 to 1000 g ai/ha. One skilled in the art can readily determine application rates and ratios of the herbicide of Formula I to the herbicide of Formula II (or IIa) as well as timing necessary for the desired level of weed control and crop safety.

The Formula I sulfonylureas (Compound 1, 2 and 3) are tested in combination with the mono isopropylamine salt of N-(phosphonomethyl)glycine (Formula II) (Compound 4).

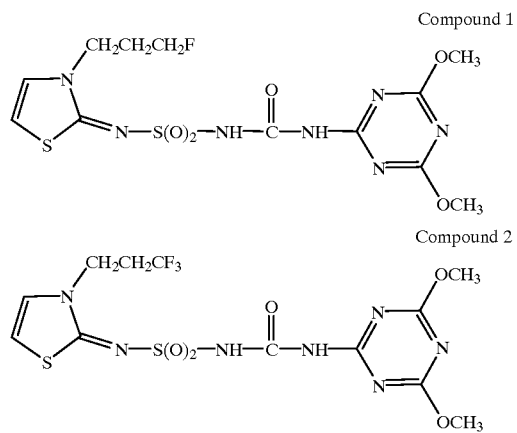

Compound 1

Compound 2

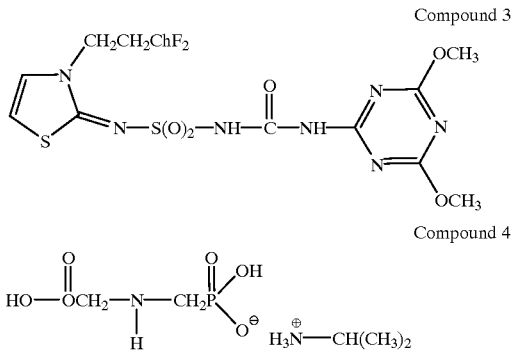

Compound 3

Compound 4

The following protocol was used for the test whose results are listed in Table A. The data demonstrate the surprising efficacy of the mixtures of this invention against specific weeds. The weed control afforded by the mixtures of this invention are not limited, however, to these species.

Test A Protocol

Kochia scoparia (KCHSC), Aegilops cylindrica (AEGCY), Avena fatua (AVEFA), Bromus tectorum (BROTE), Poa annua (POAAN), Hordeum vulgare (HORVS), Triticum aestivum (TRZAW), Helianthus annuus (HELAN) and Brassica rapa (BRSRA) were grown in a greenhouse to 2–4 leaf stage before treatment. Compound 1 was applied at 1, 2 and 4 g ai/ha postemergence. Compound 4 was applied at 250 and 500 g ai/ha postemergence. Mixtures of Compound 1 and Compound 4 were applied at 1+250, 2+250, 4+250, 1+500, 2+500, and 4+500 g ai/ha postemergence. All samples were sprayed in non-phytotoxic solvent in a volume of 310 L/ha. Assessments of weed control were made by visual inspection about 14 days following herbicide application. A visual rating system was used based on a percentage scale from 0 to 100%, relative to an adjacent untreated control plot or test area. On this scale 0% represents no visual differences relative to an untreated control, 100% represents complete kill of the given crop or weed species.

Colby's equation was used to calculate the expected additive herbicidal effect of the mixtures of Compounds 1 with Compound 4. Colby's equation (Colby, S. R. "Calculating Synergistic and Antagonistic Responses of Herbicide Combinations," Weeds, 15(1), pp 20–22 (1967)) calculates the expected additive effect of herbicidal mixtures, and for two active ingredients is of the form:

$$P_{a+b}=P_a+P_b-(P_aP_b/100)$$

wherein $P_{a+b}$ is the percentage effect of the mixture expected from additive contribution of the individual components, $P_a$ is the observed percentage effect of the first active ingredient at the same use rate as in the mixture, and $P_b$ is the observed percentage effect of the second active ingredient at the same use rate as in the mixture.

Combinations of Compounds 1 with Compound 4 are surprisingly found to provide better control of certain weeds than expected by calculation from Colby's equation, thus demonstrating synergism. Table A lists visual assessments of control of specific weeds with Compound 1 and Compound 4 applied alone as single active ingredients, applied as a mixture of the two active ingredients of Compound 1 and Compound 4, and the expected additive effect of the herbicidal mixture of Compound 1 and Compound 4 (Colby's equation). Different ratios of Compound 1 to Compound 4, and different formulation types, also provide useful weed control from the combination of the two herbicides.

TABLE A*

Effect of Compound 1 and Compound 4 as Active Ingredients Alone and in Mixture

| | Cmpd 4 | | Cmpd 1 | | | Cmpd 4 + Cmpd 1 | | | | | | | | | | | |
|---|---|---|---|---|---|---|---|---|---|---|---|---|---|---|---|---|---|
| g ai/ha Test Species | 250 Obsd | 500 Obsd | 1 Obsd | 2 Obsd | 4 Obsd | 250 + 1 Obsd | 250 + 1 Exp† | 250 + 2 Obsd | 250 + 2 Exp | 250 + 4 Obsd | 250 + 4 Exp | 500 + 1 Obsd | 500 + 1 Exp | 500 + 2 Obsd | 500 + 2 Exp | 500 + 4 Obsd | 500 + 4 Exp |
| KCHSC | 50 | 80 | 0 | 0 | 0 | 60 | 50 | 60 | 50 | 60 | 50 | 100 | 80 | 100 | 80 | 100 | 80 |
| AEGCY | 40 | 70 | 0 | 20 | 30 | 60 | 40 | 70 | 52 | 70 | 52 | 80 | 70 | 80 | 76 | 85 | 79 |
| AVEFA | 36 | 60 | 10 | 60 | 70 | 60 | 37 | 70 | 72 | 90 | 79 | 70 | 64 | 90 | 84 | 95 | 88 |
| BROTE | 60 | 85 | 30 | 50 | 60 | 80 | 72 | 90 | 80 | 95 | 84 | 98 | 90 | 100 | 93 | 100 | 94 |
| POAAN | 40 | 70 | 0 | 30 | 50 | 50 | 40 | 70 | 58 | 75 | 70 | 80 | 70 | 80 | 79 | 95 | 85 |
| HORVS | 30 | 50 | 0 | 40 | 50 | 30 | 30 | 70 | 58 | 80 | 65 | 70 | 50 | 75 | 70 | 75 | 75 |
| TRZAW | 40 | 65 | 0 | 40 | 40 | 50 | 40 | 70 | 64 | 85 | 64 | 80 | 65 | 90 | 79 | 90 | 79 |
| HELAN | 0 | 40 | 30 | 60 | 80 | 50 | 30 | 80 | 60 | 85 | 80 | 95 | 58 | 80 | 76 | 100 | 88 |
| BRSRA | 20 | 70 | 80 | 85 | 90 | 85 | 84 | 98 | 88 | 98 | 92 | 95 | 94 | 98 | 96 | 98 | 97 |

*Application rates are expressed in g ai/ha for Compound 1 and Compound 4.
Observed ("Obsd") responses are reported as percent control.
†"Exp" are expected responses calculated according to Colby, S. R. "Calculating Synergistic and Antagonistic Responses of Herbicide Combinations," Weeds, 15(1), pp 20–22 (1967).

Compounds 2, 3 and 4 are also tested alone and in combination for control of weeds troublesome to sugar beet farming. Their combinations are also found to give not only good weed control but surprisingly better control of certain weeds than expected by calculation from Colby's equation, thus demonstrating synergism.

We claim:

1. A herbicidal mixture comprising synergistic herbicidally effective amounts of a compound of Formula I

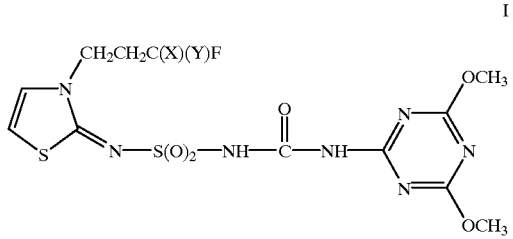

wherein X and Y are independently selected from H and F, or an agriculturally suitable salt thereof, and the compound of Formula II

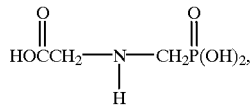

which is N-(phosphonomethyl)glycine (glyphosate) or an agriculturally suitable salt thereof.

2. The mixture of claim 1 wherein the compound of Formula I is N-(4,6-dimethoxy- 1,3,5-triazin-2-yl)-N'-[[[3-(3-fluoropropyl)-2(3H)-thiazolylidene]-amino]sulfonyl] urea.

3. The mixture of claim 2 wherein the compound of Formula II is in the form of its mono isopropylamine salt.

4. The mixture of claim 2 wherein the compound of Formula II is in the form of its mono trimethylsulfonium salt.

5. An agriculturally suitable composition for controlling the growth of undesired vegetation comprising an effective amount of the herbicidal mixtures of claim 1 and at least one of the following: surfactant, solid or liquid diluent.

6. An agriculturally suitable composition for controlling the growth of undesired vegetation comprising an effective amount of the herbicidal mixtures of claim 3 and at least one of the following: surfactant, solid or liquid diluent.

7. An agriculturally suitable composition for controlling the growth of undesired vegetation comprising an effective amount of the herbicidal mixtures of claim 4 and at least one of the following: surfactant, solid or liquid diluent.

8. The composition of claim 5 wherein the undesired vegetation is the vegetation in a crop of sugar beet plants containing at least one gene that confers resistance to glyphosate and its agriculturally suitable salts.

9. A method for controlling the growth of undesired vegetation comprising contacting the locus to be protected with a synergistic herbicidally effective amount of the composition of claim 5.

10. A method for controlling the growth of undesired vegetation comprising contacting the locus to be protected with a synergistic herbicidally effective amount of the composition of claim 6.

11. A method for controlling the growth of undesired vegetation comprising contacting the locus to be protected with a synergistic herbicidally effective amount of the composition of claim 7.

12. The method of claim 9 wherein the locus to be protected is a crop of sugar beet plants containing at least one gene that confers resistance to glyphosate and its agriculturally suitable salts.

* * * * *